United States Patent [19]

Kroll et al.

[11] Patent Number: 5,690,685
[45] Date of Patent: Nov. 25, 1997

[54] AUTOMATIC BATTERY-MAINTAINING IMPLANTABLE CARDIOVERTER DEFIBRILLATOR AND METHOD FOR USE

[75] Inventors: Mark W. Kroll, Minnetonka; Joseph S. Perttu, Chanhassen, both of Minn.

[73] Assignee: Angeion Corporation, Plymouth, Minn.

[21] Appl. No.: 549,284

[22] Filed: Oct. 27, 1995

[51] Int. Cl.$^6$ ..................................................... A61N 1/39
[52] U.S. Cl. ........................ 607/5; 607/29; 607/34
[58] Field of Search ................................ 607/2, 5, 7, 29, 607/34

[56] References Cited

U.S. PATENT DOCUMENTS

| | | |
|---|---|---|
| 4,134,408 | 1/1979 | Brownlee et al. . |
| 4,324,251 | 4/1982 | Mann . |
| 4,345,603 | 8/1982 | Schulman . |
| 4,392,193 | 7/1983 | Thompson . |
| 5,127,020 | 6/1992 | Wayne et al. . |
| 5,370,668 | 12/1994 | Shelton et al. . |
| 5,411,537 | 5/1995 | Munshi et al. . |
| 5,447,522 | 9/1995 | Chang et al. . |
| 5,458,997 | 10/1995 | Crespi et al. . |
| 5,554,174 | 9/1996 | Causey, III ................................ 607/7 |

*Primary Examiner*—William E. Kamm
*Assistant Examiner*—Kennedy J. Schaetzle

[57] ABSTRACT

A device and method for performing automatic battery maintenance as particularly applied in an implantable cardioverter defibrillator (ICD). The battery is maintained at a predetermined state-of-charge to enable charging a capacitor in the ICD to discharge high voltage pulse into a human patient via electrodes implanted in the patient.

8 Claims, 11 Drawing Sheets

AUTOMATIC BATTERY-MAINTAINING IMPLANTABLE CARDIOVERTER DEFIBRILLATOR AND METHOD FOR USE

FIELD OF THE INVENTION

The present invention deals with a battery powered implantable cardioverter defibrillator (ICD) in which the battery is maintained at a predetermined level of voltage and current capacity to reliably supply energy to charge the capacitors of the ICD on demand over an extended life of the device.

DESCRIPTION OF THE PRIOR ART

ICD's pose a unique demand on the battery power supply. The battery must be capable of operating at low current drains for long periods of time, and simultaneously be capable of providing high current pulses. The power supply must sustain the provision of the high current pulses and must be available whenever a patient requires defibrillation.

Batteries which are used in current ICD's can develop high internal impedance or equivalent series resistance (ESR) over the lifetime of the ICD. This is undesirable because a battery with an excessively high ESR will ultimately be unable to deliver sufficient current to the circuitry of the ICD leading to a potentially catastrophic result to the patient. Batteries with an ESR that is higher than normal also take longer to charge a capacitor of the ICD, thus potentially delaying the delivery of vital therapy to the patient. Under normal operations a battery in ICD should be capable of charging a capacitor in less than about fifteen seconds. Batteries with a higher than normal ESR may take five times as long.

Accordingly it is imperative to limit the development of a high ESR in ICD batteries. Generally, when a battery reforms a capacitor on a periodic basis, the battery system itself goes through a recharge cycle and this process usually eliminates some ESR that has built up in the battery system. While this technique is effective in reducing battery ESR, it can not be used more often than a monthly capacitor reforming cycle to routinely limit ESR development in the battery because the process is extremely energy-inefficient. For example, each reforming charge of the capacitor may require the withdrawal of 30–40 joules of energy from the battery. If this is performed on a regular schedule so as to limit ESR development in the battery, it would squander a large amount of battery energy.

While existing ICD batteries have proven effective, it would be desirable to improve the effectiveness of ICD batteries by limiting ESR development in ICD batteries such that the batteries are maintained at a predetermined ideal state of voltage and current delivery capacity.

SUMMARY OF THE INVENTION

The present invention maintains a battery system of an implantable cardioverter defibriliator (ICD) system by periodically measuring a state-of-charge of the battery system, and controlling the charging of a dapacitor system within the ICD from the battery system based upon the measured state-of-charge value. Preferably, the state-of-charge value is an electrical parameter value, such as a voltage value or current value. Alternatively, the state-of-charge value may be based on a charging frequency at which the battery system charges the capacitor system through a switched high voltage transformer.

In a preferred embodiment, if the state-of-charge value falls below a predetermined value, a battery loading maintenance cycle is activated. Once a battery system reaches a predetermined state-of-charge value, the loading cycle is terminated. In one embodiment, the initiation of a check of the state-of-charge value is metered by determining a given time period since the last full charge of the capacitor system has been performed.

In another alternate embodiment, the present invention detects a high ESR in the battery system during the charging of the capacitor system and, in response, modifies the charging frequencies so as to reduce the load on the battery system for a period of time sufficient for the battery system to resolve the high ESR.

DETAILED DESCRIPTION OF THE INVENTION

Figure 1:
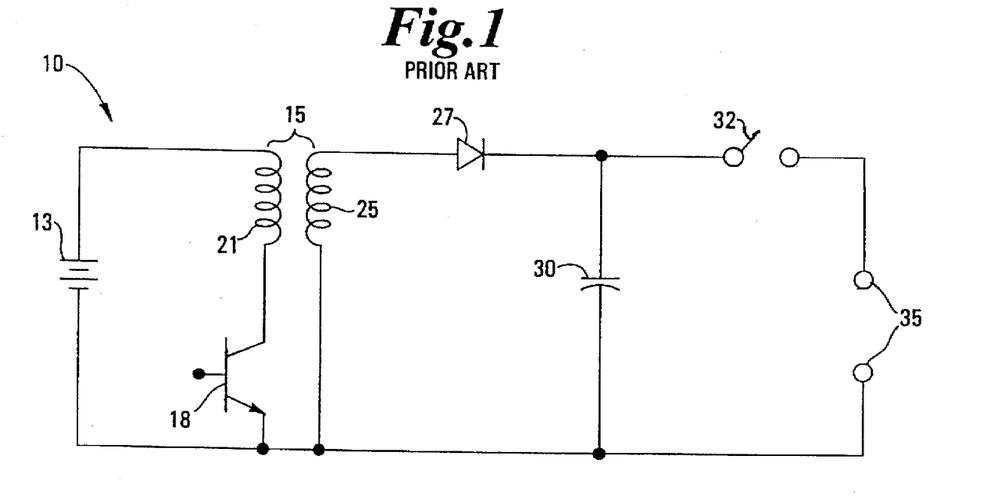
FIG. 1 is a schematic representation of a typical implantable cardioverter defibrillator (ICD) circuit.

A typical circuit for an ICD utilizing a silver vanadium oxide (SVO) battery is illustrated in FIG. 1, in which the circuitry is shown generally at 10. Battery 13 delivers a current through the primary 21 of transformer 15 upon the actuation of transistor 18. When the transistor 18 is turned off (as it is done repeatedly in typical operation), a voltage is generated across the secondary 25 of the transformer, which voltage is then directed through diode 27 to charge capacitor 30. When the capacitor 30 is charged to the required voltage, switch 32 is turned on, and the charge of the capacitor 30 is delivered to cardiac electrodes through electrodes 35.

The most common type of energy storage means in current ICD's are lithium/silver vanadium oxide (SVO) batteries. In such a battery design, the active cathode material is silver vanadium oxide. Silver vanadium oxide belongs to a class of nonstoichiometric compounds known as vanadium oxide bronzes. These compounds are semiconductors and exhibit tunnel-like crystal structures which provide diffusion paths for metal ions. It has been demonstrated that the optimum composition of the cathode material is $Ag_2V_4O_{11}$. Cell discharge takes place in multiple steps. The first two steps, which occur simultaneously, are the reduction of vanadium (V) to vanadium (IV) and the reduction of silver (I) to silver (O). The final step is the reduction of vanadium (IV) to vanadium (III). Because of the reduction of silver to the metallic state, the conductivity of the cathode increases during discharge. Stoichiometrically, one mole of $Ag_2V_4O_{11}$ can react with a total of seven moles of lithium.

Figure 2:
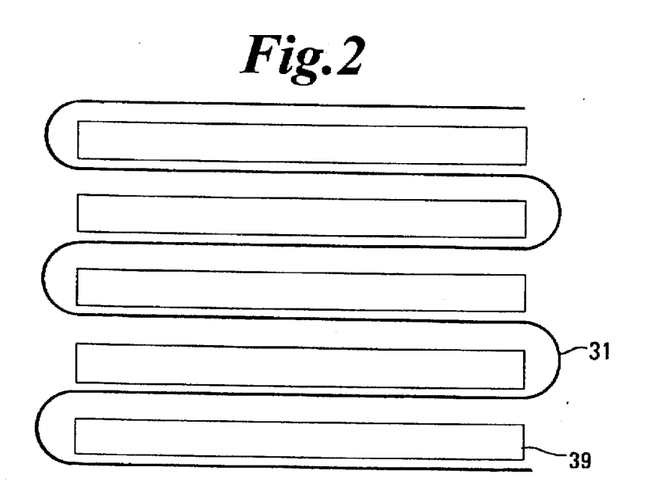
FIG. 2 is a conceptual illustration of SVO cell design, with cathode plates connected in parallel in another plane (not shown).

The anode in an SVO cell is pure lithium metal pressed onto a nickel current collector. The cathode material is a mixture of silver vanadium oxide, a Teflon binder, and a conductive carbon material. Individual cathode plates are formed by pressing the cathode material onto a metal current collector to produce a structurally sound pellet. The pellet contains 95% live cathode material. The anode 31 is folded into an "accordion" design, and individual cathode plates 39 are placed between each "fold" of the anode, as illustrated conceptually in FIG. 2. Both the anode and the cathode plates are enclosed in an organic separator for redundancy.

The chemical reactions occurring in the cell result in a constantly changing chemical composition of the cathode as the cell reaction proceeds, with a resultant change in the energetics of the reaction. This phenomenon leads to a discharge curve which exhibits plateaus at various voltages and a general gradual decline in the voltage as normal battery discharge proceeds over extended periods of time. The present invention recognizes that it is possible to assess the state of discharge of the cell by interrogating the cell voltage during discharge.

Figure 3:
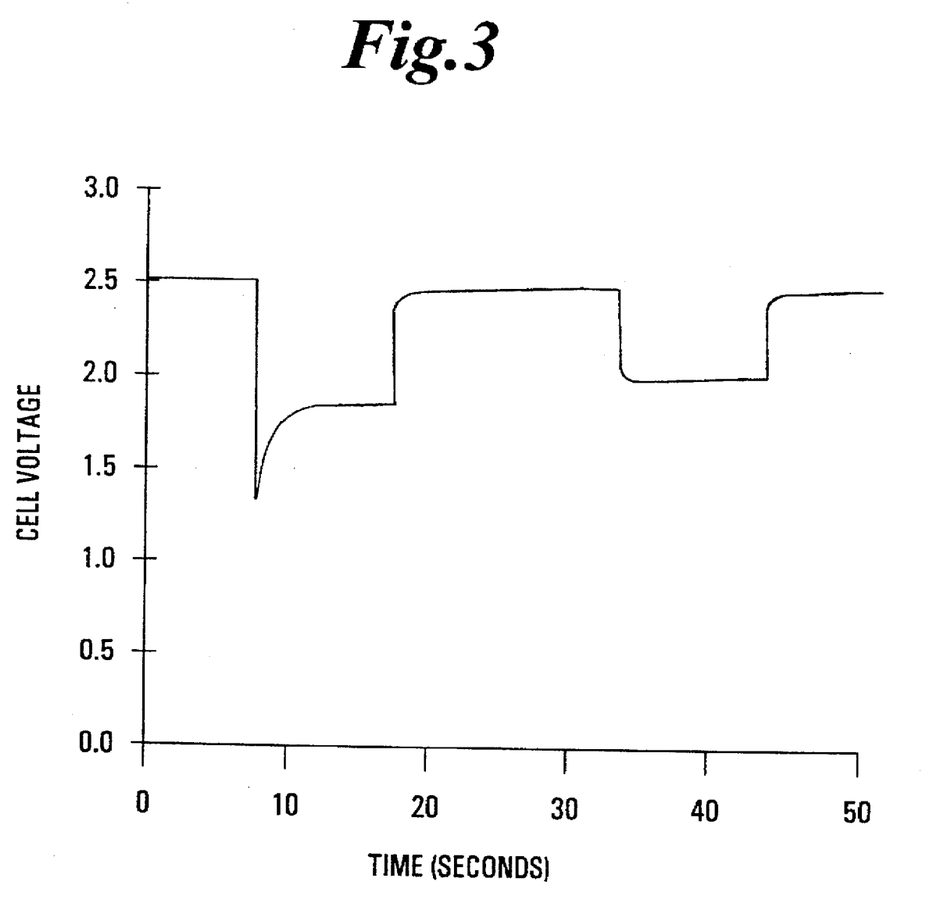
FIG. 3 is a plot of cell voltage vs. time during two simulated charging cycles illustrating a case of severe voltage delay indicative of a high ESR condition.

In FIG. 3, a plot of voltage vs. time for an ICD with circuitry of the type in FIG. 1 is shown. The battery 13 was left unattended for several months. At the start of charging, the cell had an open circuit voltage of 2.51 V which decreased to 1.35 V. During the charging, the voltage gradually recovered to 1.91 V. After a 15 s rest period, another charging cycle was initiated which had an initial voltage of 2.00 V. Thus, the battery 13 had recovered to normal operation for the second shock charging cycle. However, the charging performance during the first cycle was well below expected performance characteristics for an ICD. In a clinical setting, such a delay in application of a countershock from the ICD's capacitors could have potentially disastrous consequences for the patient in whom the device is implanted. The data of FIG. 3 illustrate the effects of failure to maintain an SVO battery and the consequent development of an equivalent series resistance (ESR) condition in the battery. The observed phenomenon during the initial charging cycle can be prevented by periodic capacitor charging, currently necessary for capacitor "reforming." However, as the design and fabrication of capacitors continues to improve, the requirement for periodic capacitor "reforming" will eventually become unnecessary, and there may be no other need for this regular and highly inefficient use of stored battery energy.

Figure 4:
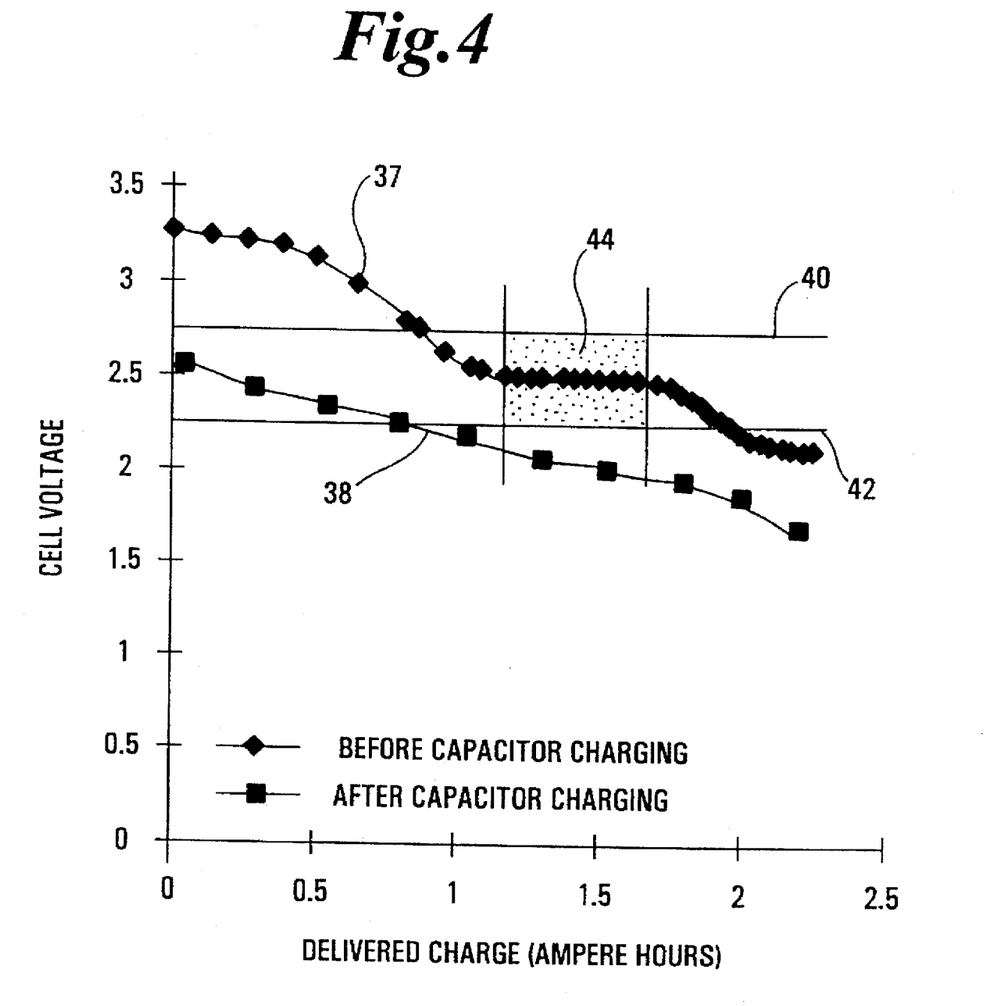
FIG. 4 is a graphical representation of battery voltage versus delivered charge for both an unloaded and a loaded circuit.

FIG. 4 illustrates the voltage change with discharge of the cell. It shows a typical discharge curve 37 for an SVO cell of nominal dimensions of 43×27×9 mm and a volume of 10.3 cm³. Curve 37 shows the results of a one year test in which the cell was subjected to a constant background load of 17.4 KΩ. (The 17.4 KΩ is a more severe load than the typical ICD monitoring circuitry provides; the one year is correspondingly much shorter than the typical ICD lifetime.) Simulating charge cycles for 4 defibrillation shocks every two months, the cell is required to produce a train of 4 pulses of 2 A each. Each pulse is of 10 s duration with a 15 s pause between pulses to accurately model the charge and retention times.

Curve 37 shows the measured voltage under the 17.4 KΩ background (monitoring) load. This quantity is referred to as the open circuit voltage as it measures the voltage while the cell is under a small or nonexistent load. (The monitoring current is very small compared to the load during capacitor charging.) Curve 37 demonstrates that the original open circuit voltage (≈3.2 volts) is level for a first period of time, then decreases for a second period of charge delivery, and then has a very flat "plateau" 44 for the next period of time. Finally, this voltage again decays at a fairly linear rate. The lower curve 38 shows the minimum voltage of the fourth pulse train of the four-pulse sequence. Curve 38 is referred to as the loaded voltage. The loaded voltage is less than the open circuit voltage by about 0.6 V since the ESR of the cell is about 0.3 Ω (and 0.6 V=2 A×0.3 Ω, by Ohm's law). The ESR represents the internal resistance of the cell which causes its loaded voltage to be less than its open circuit voltage. Curve 37 showing the "background voltage," i.e., the voltage under the 17.4 KΩ constant resistive load, decreases because the open circuit voltage is decreasing as the chemical composition of the cathode material changes. The horizontal axis of the curve shows the charge delivered by the battery in ampere hours (Ah).

FIGS. 3 and 4 also illustrate the occurrence and effects of the phenomenon referred to as voltage delay which is present under certain pulsing conditions. This phenomenon can occur during the time in which the cell is in the plateau region 44 of discharge curve 37. With voltage delay, the cell voltage at the start of a capacitor charging cycle is lower than at the end. During a 10 s charging cycle, the voltage rises from an initial minimum voltage during the first 2 or 3 s of the pulse and then continues at the typical pulse voltage throughout the rest of the 10 s interval, as illustrated in FIG. 3. This phenomenon occurs only if the time between pulses is longer than approximately two months. In other words, if the battery has not been pulsed during an interval of at least two months and if the cell is in the "flat" portion of the discharge curve, the phenomenon is observed. If the battery is pulsed monthly or more frequently, the phenomenon is not observed. The voltage delay can lead to a significant voltage decrease during the start of charging.

Figure 5:
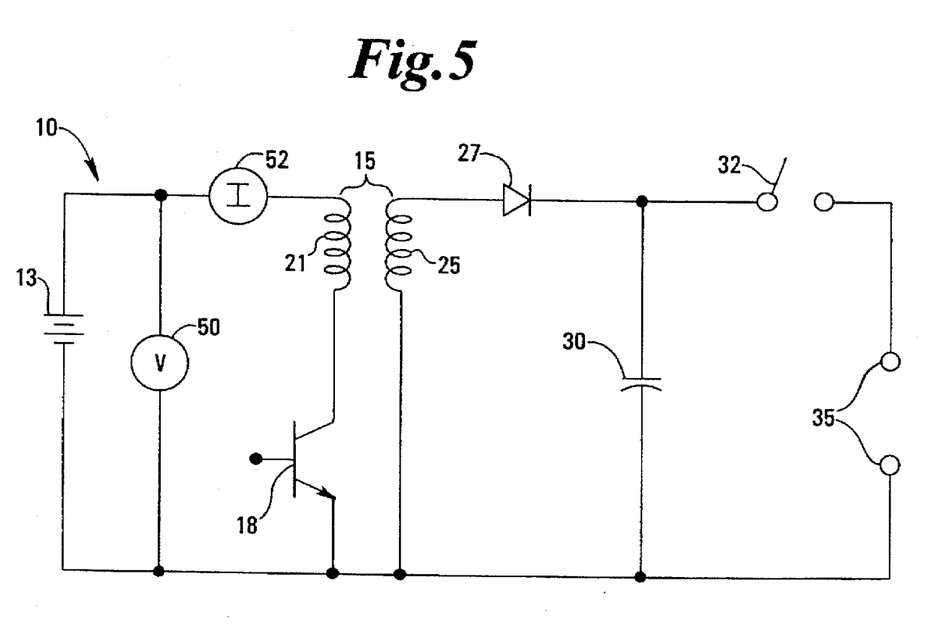
FIG. 5 is a schematic representation of an implantable cardioverter defibrillator (ICD) circuit of the present invention.

FIG. 5 provides, in schematic form, details of the ICD of the present invention. In addition to conventional ICD circuitry, such as that illustrated in FIG. 1, there is a voltmeter 50 attached to the battery 13, and a current meter 52 connected in series from the battery to the invertor. These components of the circuit are used to monitor the voltage and current to provide data for the maintenance procedures of the invention, and to provide information for scheduling of that maintenance. As will be recognized by one of ordinary skill in the digital electronic arts, the implementation of the specific circuit elements of the circuit shown generally in FIG. 5 may be achieved in a variety of ways. However, due to the specific constraints imposed by ICD design (small volume, low mass, etc.), the actual electronic implementation of the methods of the present invention will be somewhat limited. By way of example, and without limitation as to the practice of the methods of the present invention, possible implementations of various electronic circuit elements compatible with the practice of the present invention are provided in the accompanying figures and described in more detail below.

Figure 6:
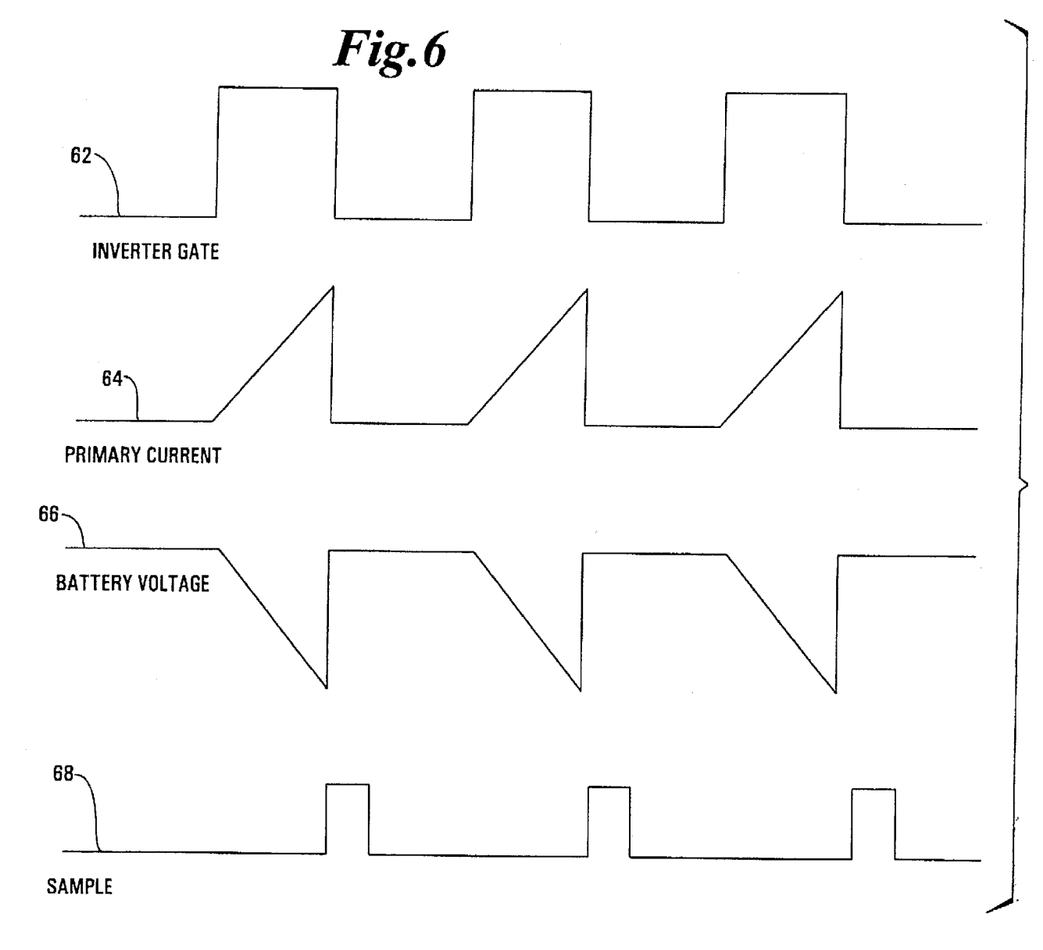
FIG. 6 provides a timing diagram for the functioning of an electronic circuit in accord with the practice of the present invention.

Referring to FIG. 6, there is provided a timing diagram for the functioning of a circuit in accord with the practice of the present invention. The top trace 62 represents the status of the invertor switch drive line 18 in the detail in the general schematic of FIG. 5. The next trace 64 represents the status of the primary current during initiation of a typical charging cycle in the method of the invention. Trace 66 indicates the condition of the battery voltage during the corresponding time period, and trace 68 indicates the specific timing of the sampling necessary to the practice of the invention.

Figure 7:
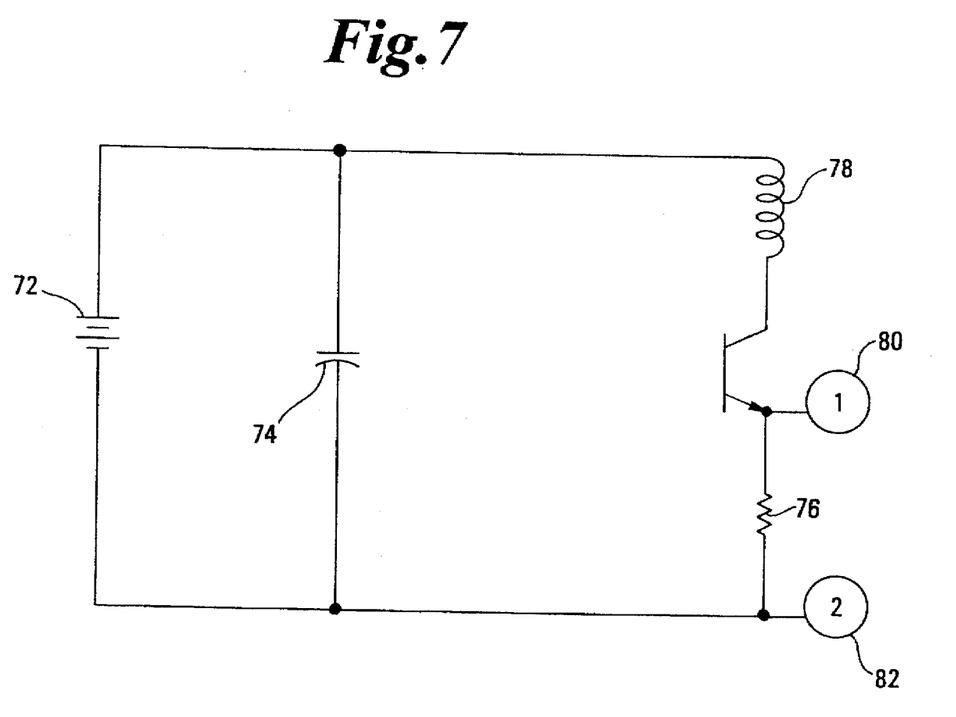
FIG. 7 illustrates a portion of the invertor circuitry of a device embodying the present invention.

Referring now to FIG. 7, there is provided a level of detail to the general circuit of FIG. 5 illustrating a portion of the invertor circuitry. FIG. 7 illustrates a battery 72 and a capacitor 74 in series, along with transistor 77. Also shown is resistor 76, which functions as a sensing resistor and is characterized by a relatively low impedance, on the order of 20–50 m$\Omega$. Contact points 80, 78 are utilized by appropriate digital or analog circuitry to establish either voltage or current measurements across sensing resistor 76.

Figure 8:
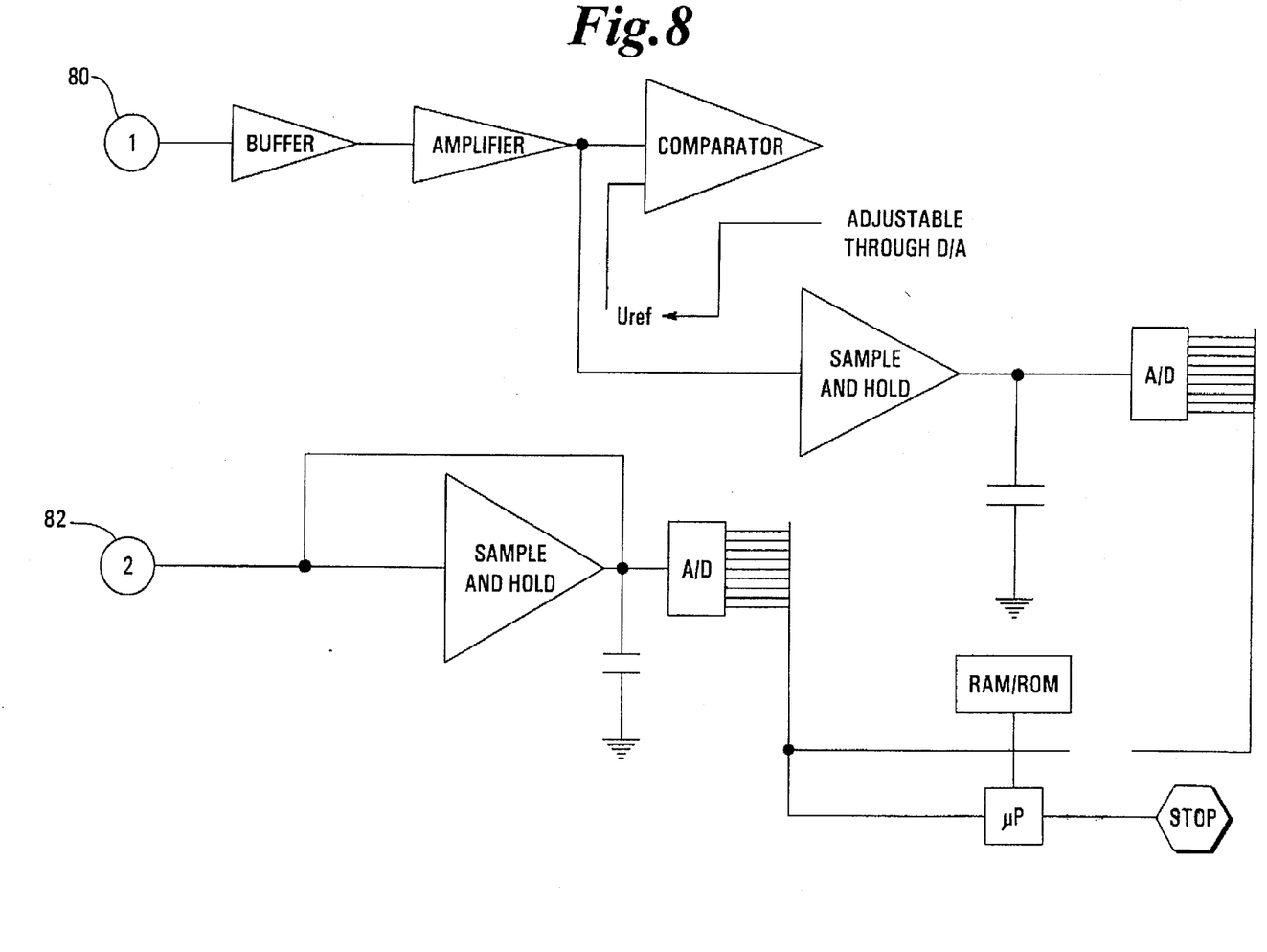
FIG. 8 is an illustration of a digital control circuit complementary to that shown in FIG. 7.
Figure 9:
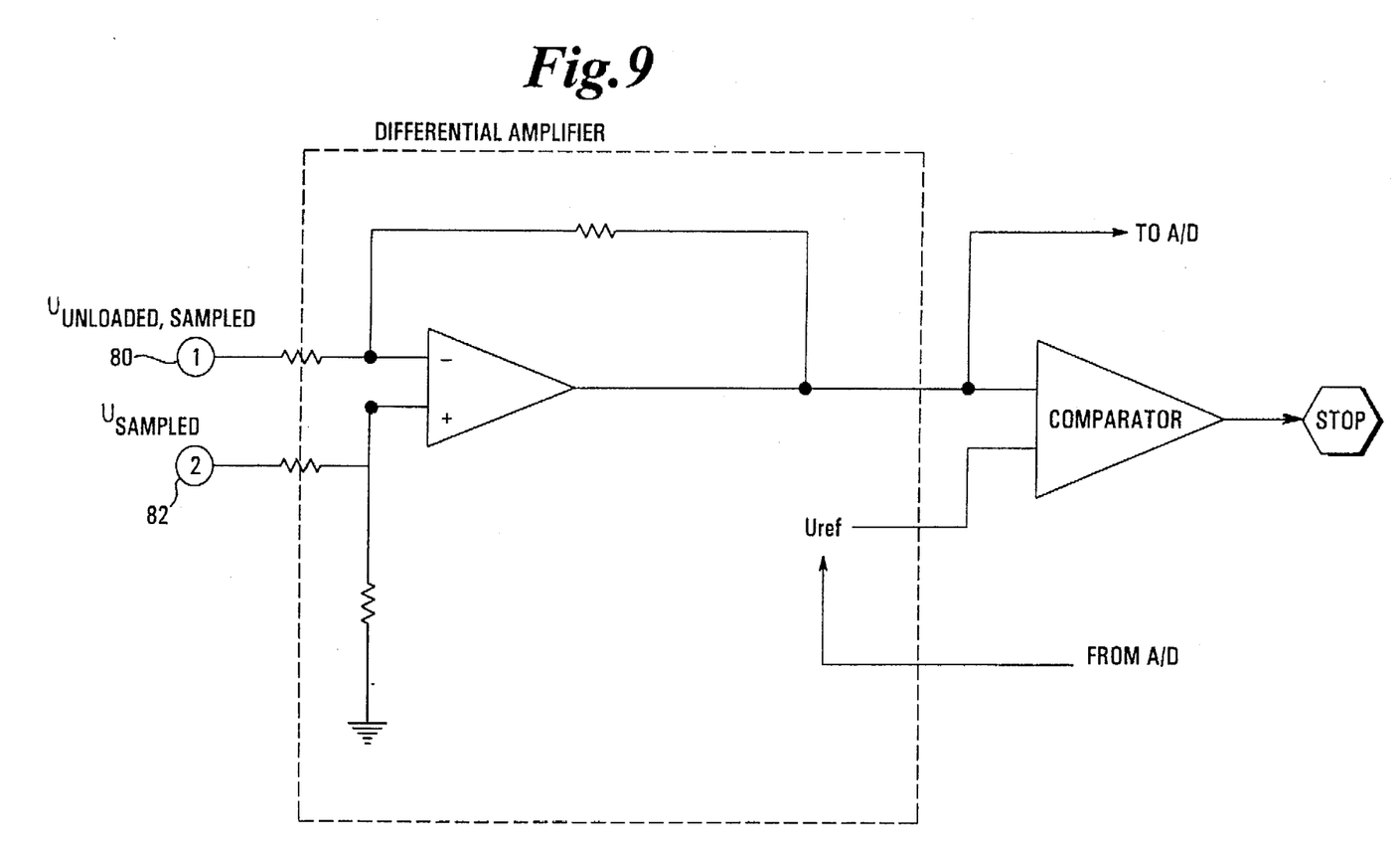
FIG. 9 illustrates a portion of an analog circuit capable of functioning in accord with the present invention.

Illustrated in FIG. 8 is a digital circuit complementary to that shown in FIG. 7. Contacts 80 and 78 are common to the correspondingly numbered elements of FIG. 7. FIGS. 7 and 8, taken in combination, present a fully digital implementation of the device and method of the present invention. However, as will be recognized by one of ordinary skill in the appropriate art, the present invention can be practiced through the use of analog circuitry as well. By way of example only, and without limitation, FIG. 9 provides generally a portion of an analog circuit capable of functioning in accord with the present invention.

Referring again to FIG. 4, the voltage threshold line 40 is shown as approximately 2.75 volts. It is recognized that the temporary increase in ESR occurs during the plateau period 44. In order to isolate this period, and to do so conservatively, the present invention provides two voltage thresholds 40 and 42. When the voltage on the cell is below that of threshold 40 ($\approx$2.75 volts), and above that of voltage threshold 42 ($\approx$2.4 volts), the battery is in its plateau region, indicating the potential need for maintenance. It should be appreciated that the voltage data shown in FIG. 4 from which the threshold voltages for the practice of the present invention are determined are presented for example purposes only, and should not be taken as absolutes to be applied in every situation. The data for FIG. 4 and the threshold voltages utilized in the discussion herein are representative of a particular ICD and, as such, will need to be adjusted for varying devices, depending on characteristics of the circuitry and batteries involved, a task that is well within the scope of one of ordinary skill in the appropriate art.

Figure 10:
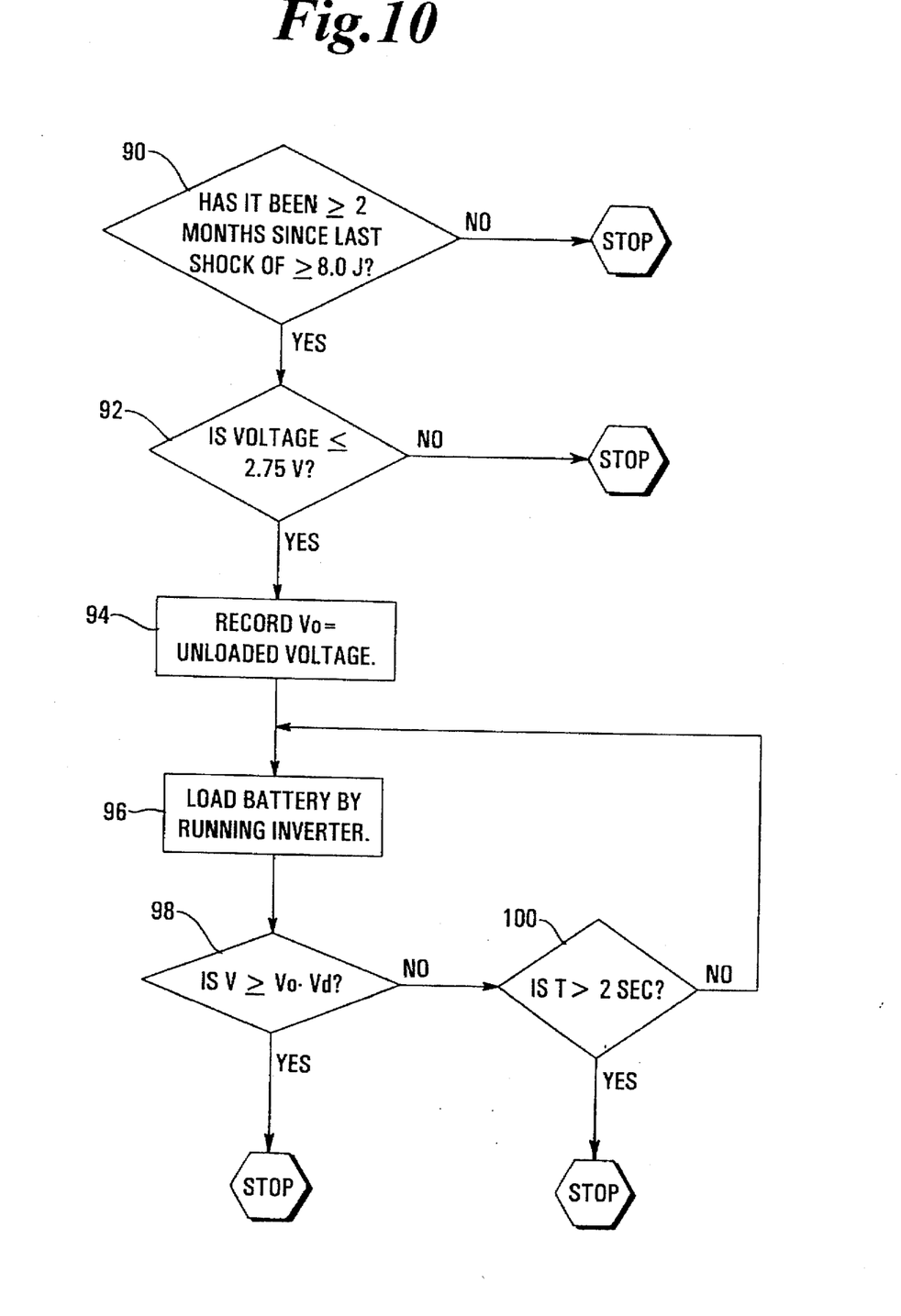
FIG. 10 is an illustration, as represented by a flow chart, of an embodiment of the present invention.

Referring now to FIG. 10, there is provided, in flow chart form, the maintenance scheduling and operation of an embodiment of the method of the present invention. The flow chart represents a sequence of events and decisions that would preferably be acted upon on at least a daily basis. However, as would be recognized by one of skill in the appropriate art, the current state of digital circuitry design and control would permit monitoring of the state of the battery according to the present invention over a wide range of programmable time intervals.

In the first step 90 of the method of the present invention, the ICD would determine the time elapsed since the last shock of significant energy. As defined in this embodiment, the significant energy at decision point 90 is a shock greater than or equal to 8 joules. As would be recognized in the art, this could be more or less depending upon the type of battery and the design of the charging circuitry. If the circuit determines at decision point 90 that the time since last threshold shock is less than two months, then the maintenance procedure stops. If there is an indication that it has been greater than two months since the last threshold shock, then the maintenance process continues.

The next decisional point of the method is a voltage comparison 92. The instantaneous voltage of the battery is measured by volt meter 50 (see FIG. 5) and compared to a pre-determine d threshold voltage 40 (see FIG. 4) which, by way of example, is 2.75 volts. If the voltage is greater than the 2.75 volts of this example, then the maintenance procedure stops, as it is known that the battery is not in its plateau region (see FIG. 3), and is not in danger of developing an unacceptably high ESR. If the voltage comparison 90 determines that the instantaneous battery voltage is less than the pre-determined threshold, then the maintenance procedure continues. The method of the present invention as represented in FIG. 10 is a somewhat simplified embodiment of the invention in that the decisional process employed in the method makes use only of the upper threshold voltage level 40 of FIG. 4. Thus, this embodiment does not make use of the additional threshold voltage 42 of FIG. 4. The advantage of an alternative embodiment involving checking the threshold line 42 is that such an additional step would eliminate the use of scarce energy for battery maintenance when the battery is very near the end of its useful life. The disadvantage of this approach is additional complexity for measuring the battery voltage when the device is very close to the end of its life.

According to FIG. 10, the next step 94 involves the recording and storing of $V_0$ which is the instantaneous unloaded voltage that was measured in step 92. The next step in the method involves starting the battery loading cycle 96 which charges the capacitors. During this battery loading cycle, there are two items that are checked on a continual basis. A voltage comparison 98 is performed continuously to compare the instantaneous output voltage of the cell to the previously measured unloaded voltage (Vo), corrected for an allowed voltage drop ($V_d$). If it is determined that the instantaneous output voltage is greater than the corrected unloaded voltage, then the battery has had sufficient maintenance, and the maintenance procedure terminates. If the voltage is below this level, then maintenance capacitor loading must continue.

The next step of the method is a time comparison 100. The method is designed to initiate a charging cycle of a maximum duration of two seconds. This is based on the assumption, derived from experimental observations, that charging sufficient to correct for temporary ESR conditions is generally achieved within two seconds. In comparison, the capacitor "reforming" charge pulse is typically of ten seconds duration. Thus, if the time comparison 100 determines that the charging cycle has not yet been in progress for two seconds, then the method continues. However, once the two second period has passed, then the method terminates in accordance with the above-stated empirically-based assumption.

The pre-determined voltages, energies, and time limits that are involved in the method of the present invention as represented in FIG. 10 are all variables, recognizably dependant upon the size of the battery and the circuitry. For example, as one of skill in the art would recognize, a maintenance cycle length of up to four months may be acceptable. A charge time of one second may also be acceptable for maintenance. Thus, the variable values presented here are presented solely for the purpose of example, and are not intended in any way as a limitation on the practice of the method of the present invention.

Figure 11:
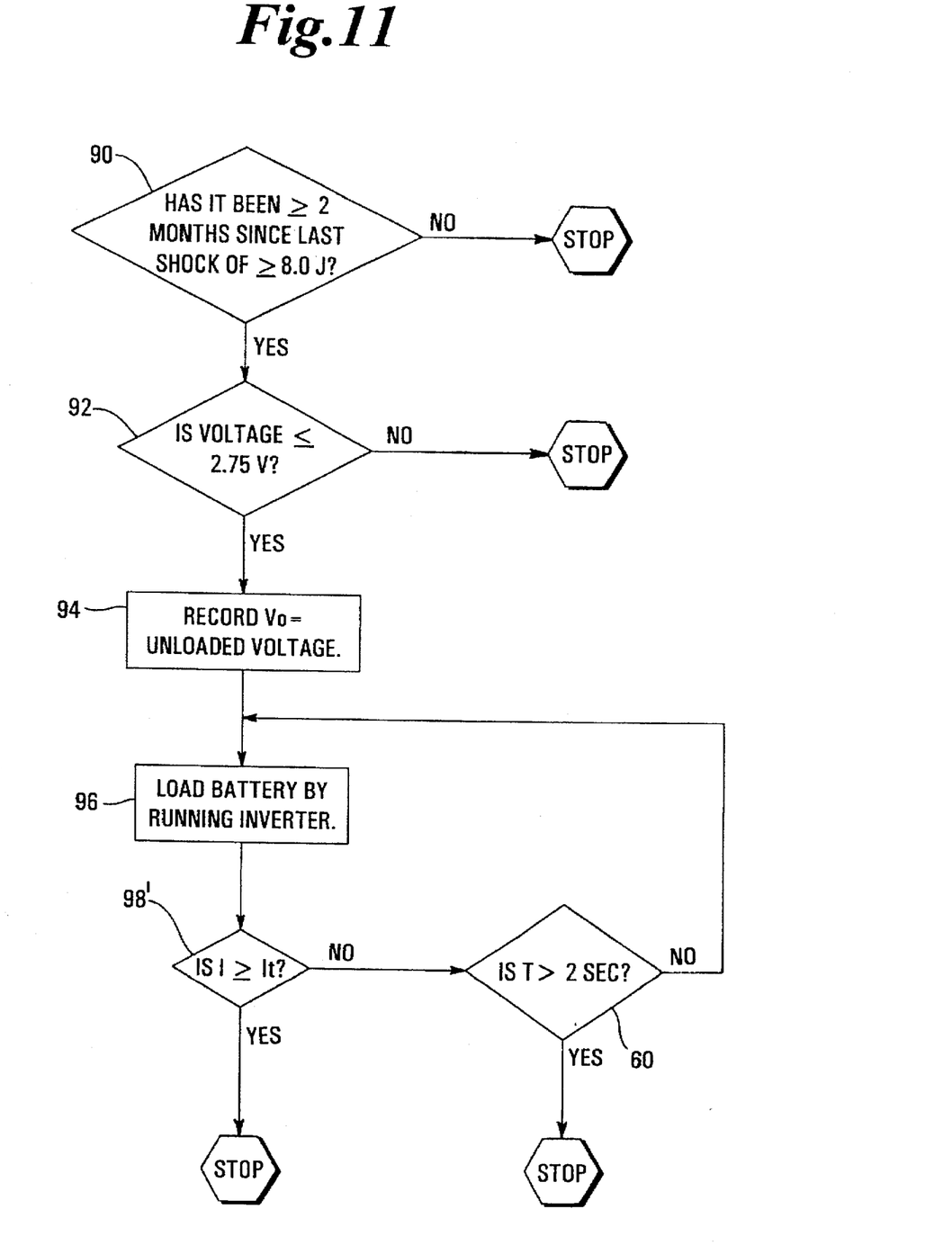
FIG. 11 is an illustration, as represented by a flow chart, of an alternative embodiment of the present invention.

Referring now to FIG. 5 current meter 52 has two uses. The first is as an alternative, in another embodiment of the invention, for the voltage measurement of step 98 in FIG. 10. This alternative embodiment, as illustrated in FIG. 11, is possible because another indicator of the recovery of a battery is the determination of whether the battery is capable of delivering a current in excess of a minimum threshold level. Thus, in this alternate embodiment, during the maintenance, loading period, the current through meter 52 is monitored continuously at step 98 of FIG. 11. When the monitoring indicates that the current is in excess of a predetermined threshold level, then the maintenance procedure is terminated.

Figure 12:
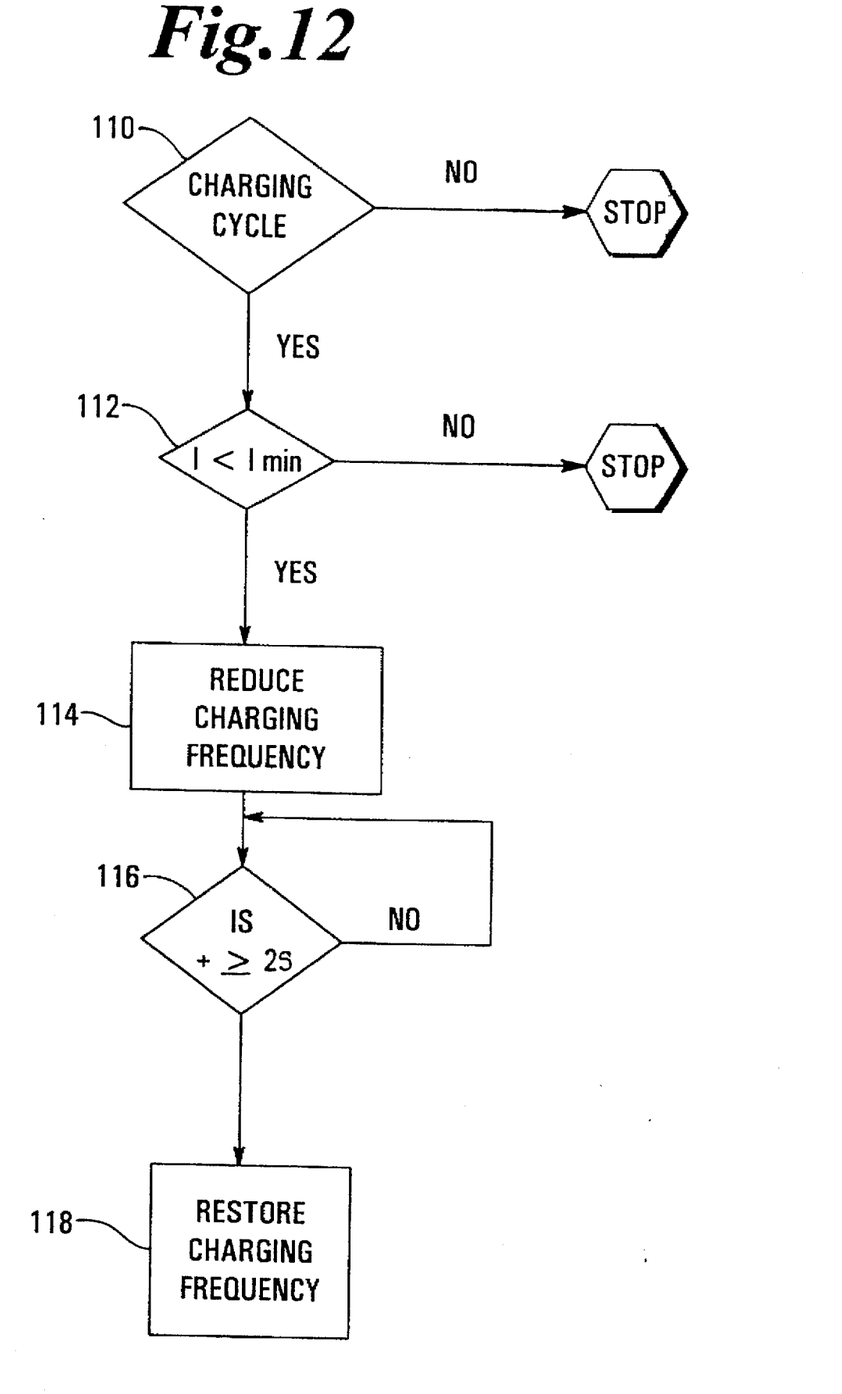
FIG. 12 is an illustration, as represented by a flow chart, of an alternative embodiment of the present invention.

The alternative purpose of current meter 52 is for emergency backup determination of the maintenance state of the battery. If, for some reason, the battery maintenance was unsuccessful, then a high ESR could develop. This could lead to a reduction in output current capability which could prevent the delivery of effective therapy until removal and maintenance of the battery. If during the capacitor charging for a normal shock, the current meter 52 detects a reduction in output current below the minimum allowable level, then this would indicate that a high ESR condition exists. Alternatively, the same result could also indicate that the battery could be past the period of its useful life, although there are generally available a number of means to monitor a battery for that condition, such as early low voltage warnings and replacement. With this low current warning, the circuitry is then instructed to pulse the transistor 18 at a lower rate to minimize the load on the battery 13 until reconditioning was completed. This would generally require only a few seconds, after which time the circuitry could resume operation at full current. FIG. 12 shows this embodiment. The process is started at step 110 if a charging cycle is occurring. At step 112, a minimum current determination is made. If the minimum current is not present, the charging frequency is decreased. A predetermined time period is measured at step 116, shown to be 2 s although other times may be indicated depending upon the circuitry and the battery. Afterward, the charging frequency is restored to its original value. Alternatively, upon sensing a lower current or high ESR, the charging frequency could be reduced and then gradually ramped back up to the normal charging frequency.

Having thus described the preferred embodiments of the present invention, those of skill in the art will readily appreciate the many other embodiments which can be employed within the scope of the claims provided below.

What is claimed is:

1. A method for maintaining a battery system in a defibrillator implanted within a human patient comprising the device-implemented steps of:

(a) periodically measuring an electrical parameter value of the battery system;

(b) comparing the measured electrical parameter value to a pre-determined electrical parameter comparison value; and (c) if the measured electrical parameter value is less than the pre-determined electrical parameter comparison value, initiating a battery loading maintenance cycle,
   (a1) periodically determining a time interval corresponding to a most recent occurrence of a charging cycle by the battery system in the defibrillator;
   (a2) if the time interval of step (a1) is greater than or equal to a pre-determined battery maintenance interval, measuring the electrical parameter value of the battery system.

2. A method for maintaining a battery system in a defibrillator implanted within a human patient comprising the device-implemented steps of:

(a) periodically measuring an electrical parameter value of the battery system;

(b) comparing the measured electrical parameter value to a pre-determined electrical parameter comparison value; and (c) if the measured electrical parameter value is less than the pre-determined electrical parameter comparison value, initiating a battery loading maintenance cycle, wherein step (b) comprises the steps of:

(b1) comparing the measured electrical parameter value to a first and a second pre-determined electrical parameter comparison value; and (b2) ceasing the method if the electrical parameter value of the battery system is less than the second pre-determined electrical comparison value.

3. A method for maintaining a battery system in a defibrillator implanted within a human patient comprising the device-implemented steps of:

(a) periodically measuring an electrical parameter value of the battery system;

(b) comparing the measured electrical parameter value to a pre-determined electrical parameter comparison value; and (c) if the measured electrical parameter value is less than the pre-determined electrical parameter comparison value. initiating a battery loading maintenance cycle, wherein the battery loading maintenance cycle of step (c) comprises the steps of:

(c1) initiating a battery loading cycle timer to measure an elapsed time of the battery loading maintenance cycle;

(c2) initiating a battery loading cycle;

(c3) measuring an instantaneous electrical parameter value during the battery loading cycle;

(c4) comparing a corrected electrical parameter value to the instantaneous electrical parameter value;

(c5) ceasing the battery loading cycle if the instantaneous electrical parameter value if greater than the corrected electrical parameter value;

(c6) ceasing the battery loading cycle if the battery loading cycle timer indicates that the elapsed time of the battery loading cycle is greater than a pre-determined battery loading cycle cutoff time; and (c7) repeating steps (c3) through (c7).

4. A method for using a battery system to charge a capacitor system in a defibrillator implanted within a human patient, wherein the method comprises the steps of:

(a) initiating a capacitor charge cycle to charge the capacitor system using the battery system at a given charging frequency;

(b) measuring an electrical parameter value of the battery system;

(c) comparing the electrical parameter value to a pre-determined electrical parameter comparison value;

(d) if the electrical parameter value is less than the pre-determined electrical parameter comparison value,
   (d2) interrupting the capacitor charge cycle;
   (d2) decreasing the charging frequency;
   (d3) charging the capacitor system using the battery system at the lower charging frequency established in step (d2); and
   (d4) repeating steps (b) through (d) until the measured electrical parameter value is greater than the pre-determined electrical parameter comparison value; and (e) continuing the charging cycle at the given charging frequency.

5. A method for optimizing maintenance of a battery system in a cardioverter defibrillator implanted within a human patient, wherein the method comprises the steps of:

a. comparing a first time value corresponding to an instantaneous time to a second time value corresponding to a most recent occurrence of a discharge of stored current from the battery system, provided that an energy equivalent of the discharge was greater than or equal to a pre-determined discharge energy threshold value;

b. ceasing the method unless the comparison of step (a) yields a time difference between the first and second time values greater than or equal to a pre-determined battery maintenance interval value;

c. measuring a first electrical parameter value of the battery system;

d. comparing the first measured electrical parameter value to a first pre-determined electrical parameter comparison value;

e. ceasing the method unless the first measured electrical parameter value is less than or equal to the first pre-determined electrical parameter comparison value;

f. initiating a battery loading maintenance cycle;

g. measuring a second electrical parameter value of the battery system during the battery loading maintenance cycle;

h. comparing the second measured electrical parameter value to a second electrical parameter comparison value;

i. ceasing the method unless the second measured electrical parameter comparison value is greater than the first measured electrical parameter value; and j. repeating steps through.

6. The method of claim 5, wherein the method includes the additional steps, performed subsequent to step (e) and prior to step (f) of:

(1) comparing the measured electrical parameter value to a third pre-determined electrical parameter comparison value; and (2) ceasing the method unless the measured electrical parameter value is greater than or equal to the third pre-determined electrical parameter comparison value.

7. An automatic power maintenance and replenishment cycle device for a battery system coupled to a self-contained implantable cardioverter defibrillator (ICD) unit wherein the ICD unit includes the battery system, a capacitor system, a sensing system and a control system which in combination supply high voltage pulses to arrest cardiac arrhythmia in a human patient the high voltage being supplied to the patient by means of implantable electrodes having electrical contact with the ICD unit comprising:

means for measuring power levels in the battery in combination with means for comparing said power levels with a predetermined electrical parameter comparison value;

means for initiating a replenishment cycle of the battery to a level of said predetermined electrical parameter comparative value based on a predetermined inverter frequency; and means for terminating the replenishment cycle;

said replenishment cycle device being in electrical communication with and housed by said ICD unit.

8. A device to automatically charge a battery system, having a voltage leakage, to attenuate equivalent series resistance and thereby insure a competent state-of-charge inventory in the battery at all times, such that a capacitor system in an implantable cardioverter defibrillator (ICD) unit can be optimally charged on demand, the ICD unit containing the battery system, the capacitor system, a sensing system and a control system such that when a high voltage pulse is needed to arrest cardiac arrhythmia in a human patient, the control system can selectively discharge the high voltage pulse in the capacitor system through electrodes disposed in the human patient comprising:

means for measuring the state-of-charge of the battery;

means for comparing power loss of the battery due to said voltage leakage with said competent state-of-charge;

means for initiating an automatic charge to the battery based on a predetermined inverter frequency;

means for terminating said automatic charge to the battery;

said ICD unit including the systems therein being in electrical communication with and housing said device to automatically charge the battery system.

* * * * *